(12) United States Patent
Mostafavi

(10) Patent No.: US 10,737,118 B2
(45) Date of Patent: Aug. 11, 2020

(54) SYSTEMS AND METHODS FOR PATIENT POSITION MONITORING

(71) Applicant: Varian Medical Systems, Inc., Palo Alto, CA (US)

(72) Inventor: Hassan Mostafavi, Los Altos, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 0 days.

(21) Appl. No.: 15/121,290

(22) PCT Filed: Mar. 3, 2015

(86) PCT No.: PCT/US2015/018520
§ 371 (c)(1),
(2) Date: Aug. 24, 2016

(87) PCT Pub. No.: WO2015/134521
PCT Pub. Date: Sep. 11, 2015

(65) Prior Publication Data
US 2017/0014648 A1  Jan. 19, 2017

Related U.S. Application Data

(60) Provisional application No. 61/947,402, filed on Mar. 3, 2014.

(51) Int. Cl.
*A61N 5/10* (2006.01)
*A61B 5/00* (2006.01)
(Continued)

(52) U.S. Cl.
CPC .......... *A61N 5/1069* (2013.01); *A61B 5/0037* (2013.01); *A61B 5/0555* (2013.01); *A61B 5/1114* (2013.01); *A61B 5/1128* (2013.01); *A61N 5/1081* (2013.01); *A61N 2005/1087* (2013.01)

(58) Field of Classification Search
None
See application file for complete search history.

(56) References Cited

U.S. PATENT DOCUMENTS 5,623,560 A     4/1997  Nakajima et al.
6,621,889 B1 *  9/2003  Mostafavi .............. A61B 6/541
                                                              378/65

(Continued)

OTHER PUBLICATIONS

Tiangang et al, 3D Surface Reconstruction Based on Kinect Sensor, International Journal of Computer Theory and Engineering, vol. 5, No. 3, Jun. 2013.*

(Continued)

*Primary Examiner* — Andrae S Allison
(74) *Attorney, Agent, or Firm* — Vista IP Law Group, LLP

(57) ABSTRACT

A method of monitoring a patient includes: obtaining an input image having a plurality of regions of interest by a processing unit; and determining a plurality of positions for the respective plurality of regions of interest by the processing unit; wherein the act of determining the plurality of positions comprises: accessing a plurality of templates; comparing the plurality of templates with respective areas in the input image using a comparator in the processing unit; and determining the plurality of positions based at least in part on a result of the act of comparing.

45 Claims, 12 Drawing Sheets

(51) Int. Cl.
*A61B 5/055* (2006.01)
*A61B 5/11* (2006.01)

(56) References Cited

U.S. PATENT DOCUMENTS

| | | | | |
|---|---|---|---|---|
| 6,690,965 B1* | 2/2004 | Riaziat | ............. | A61B 6/463 378/62 |
| 6,782,287 B2* | 8/2004 | Grzeszczuk | ............ | A61B 90/36 600/424 |
| 6,842,502 B2* | 1/2005 | Jaffray | ............. | A61B 6/032 378/19 |
| 7,133,537 B1* | 11/2006 | Reid | ............. | G06T 7/254 382/103 |
| 9,724,540 B2* | 8/2017 | Mori | ............. | A61N 5/1049 |
| 9,956,427 B2* | 5/2018 | Mori | ............. | A61N 5/1049 |
| 2002/0045817 A1* | 4/2002 | Ichihashi | ............ | A61B 6/4233 600/425 |
| 2003/0086596 A1* | 5/2003 | Hipp | ............. | G06T 7/0012 382/128 |
| 2004/0087852 A1* | 5/2004 | Chen | ............. | A61B 6/4405 600/407 |
| 2004/0218792 A1* | 11/2004 | Spoonhower | ......... | A61B 5/0084 382/128 |
| 2005/0002546 A1* | 1/2005 | Florent | ............ | G06T 5/50 382/128 |
| 2005/0031176 A1* | 2/2005 | Hertel | ............. | G06T 7/33 382/128 |
| 2005/0053196 A1* | 3/2005 | Mostafavi | ............ | A61B 6/4441 378/98.12 |
| 2005/0054916 A1* | 3/2005 | Mostafavi | ............ | A61B 6/504 600/427 |
| 2005/0129305 A1 | 6/2005 | Chen et al. | | |
| 2008/0278584 A1 | 11/2008 | Shih et al. | | |
| 2009/0149741 A1 | 6/2009 | Heigl | | |
| 2010/0061596 A1* | 3/2010 | Mostafavi | ............ | A61B 5/113 382/107 |
| 2010/0166072 A1* | 7/2010 | Bukin | ............. | H04N 19/533 375/240.16 |
| 2010/0198112 A1* | 8/2010 | Maad | ............. | A61B 6/0457 600/595 |
| 2011/0178783 A1 | 7/2011 | Smith et al. | | |
| 2017/0043184 A1* | 2/2017 | Mori | ............. | A61N 5/1049 |

OTHER PUBLICATIONS

Dawson et al, Advances in Image-Guided Radiation Therapy, Journal of Clinical Oncology, vol. 25 No. 8 Mar. 10, 2007.*

Coudert et al, Back-projection algorithm with misalignment corrections for 2D3C stereoscopic PIV, Institute of Physics Publishing Meas. Sci. Technol. 12 (2001) 1371-1381.*

Prince, Jerry L. "A convolution backprojection formula for three-dimensional vector tomography." Image Processing, 1994. Proceedings. ICIP-94., IEEE International Conference. vol. 2. IEEE, 1994.*

Wiesner et al, Monitoring Patient Respiration using a Single Optical Camera, Proceedings of the 29th Annual International Conference of the IEEE EMBS Cité Internationale, Lyon, France, Aug. 23-26, 2007. (Year: 2007).*

M. A. Gennert et al, "Feasibility of tracking patient respiration during cardiac SPECT imaging using stereo optical cameras," 2003 IEEE Nuclear Science Symposium. Conference Record (IEEE Cat. No. 03CH37515), Portland, OR, USA, 2003, pp. 3170-3172 vol. 5. (Year: 2003).*

Goyal, Shikha, and Tejinder Kataria. "Image guidance in radiation therapy: techniques and applications." Radiology research and practice2014 (2014). (Year: 2014).*

Cui, Ying, et al. "Multiple template-based fluoroscopic tracking of lung tumor mass without implanted fiducial markers." Physics in Medicine & Biology 52.20 (2007): 6229. (Year: 2007).*

Spinczyk, Dominik, Adam Karwan, and Marcin Copik. "Methods for abdominal respiratory motion tracking." Computer Aided Surgery 19.1-3 (2014): 34-47. (Year: 2014).*

Baroni, Guido, et al. "Integration of enhanced optical tracking techniques and imaging in IGRT." Journal of radiation research 48. Suppl_A (2007): A61-A74. (Year: 2007).*

International Search Report and Written Opinion dated Jul. 27, 2015 for corresponding PCT Patent Application No. PCT/US2015/018520, 9 pages.

European Examination Report dated Oct. 10, 2018 for corresponding EP Application No. 15758141.4, 5 pages.

Supplementary European Search Report dated Oct. 27, 2017 for corresponding EP Patent Application No. 15758141.4.

Sharp et al. "Anatomic feature-based registration for patient set-up in head and neck cancer radiotherapy: Anatomic feature-based registration", Physics in Medicine and Biology, Institute of Physics Publishing, Bristol GB, vol. 50, No. 19, Oct. 7, 2005.

Cui et al. "Multiple template-based fluoroscopic tracking of lung tumor mass without implanted fiducial markers", Physics in Medicine and Biology, Institute of Physics Publishing, Bristol GB, vol. 52, No. 20, Oct. 21, 2007.

First Office Action dated Feb. 3, 2019 for corresponding Chinese Patent Application No. 201580011442.9.

First Indian Examination Report dated Aug. 19, 2019 for corresponding Indian Patent Application No. 201647027669.

Intention to Grant dated Sep. 20, 2019 for corresponding EP Application No. 15758141.4.

* cited by examiner

SYSTEMS AND METHODS FOR PATIENT POSITION MONITORING

RELATED APPLICATION DATA

This application is the national stage of International Patent Application No. PCT/US2015/018520, filed Mar. 3, 2015, pending, which claims priority to and the benefit of U.S. Provisional Patent Application No. 61/947,402, filed on Mar. 3, 2014. The entire disclosures of all of the above applications are expressly incorporated by reference herein.

FIELD

The field of the application relates to systems and methods for monitoring a patient.

BACKGROUND

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. During a radiation therapy, a radiation source may be rotated around a patient to deliver radiation from different angles at target region inside the patient. The radiation source may be mounted on an arm or a ring gantry.

Also, radiation may be used for imaging purposes. For example, a computed tomography (CT) machine has a radiation source configured to rotate around a patient while delivering imaging radiation from different gantry angles around the patient.

In both treatment and imaging procedures, it may be desirable to monitor positions of different parts of the patient. Thus, applicant of the subject application determines that it may be desirable to provide a patient monitoring system that can simultaneously monitor different parts of a patient.

SUMMARY

A method of monitoring a patient includes: obtaining an input image having a plurality of regions of interest by a processing unit; and determining a plurality of positions for the respective plurality of regions of interest by the processing unit; wherein the act of determining the plurality of positions comprises: accessing a plurality of templates; comparing the plurality of templates with respective areas in the input image using a comparator in the processing unit; and determining the plurality of positions based at least in part on a result of the act of comparing.

Optionally, the act of comparing comprises performing template matching using the input image and a plurality of templates for the respective regions of interest.

Optionally, the act of comparing comprises performing a plurality of cross correlations between the areas in the input image and the plurality of templates.

Optionally, the method further includes creating the plurality of templates.

Optionally, the act of creating the plurality of templates comprises: obtaining a reference image; determining a plurality of points in the reference image; and generating the plurality of templates using pixels in the reference image, such that the templates have respective coordinates that correspond with respective positions of the determined points in the reference image.

Optionally, the act of determining the plurality of points in the reference image comprises: determining a plane above a patient support supporting the patient; determining points on the plane; and transferring the plurality of points on the plane to a pixel domain of the reference image.

Optionally, the act of determining the plurality of points in the reference image comprises: obtaining a depth image; processing the depth image to determine a plurality of points in the depth image; and transferring the plurality of points in the depth image to a pixel domain of the reference image.

Optionally, the act of processing the depth image comprises thresholding depth values in the depth image so that pixels with depths corresponding to points within a virtual box surrounding the patient are included as candidates for the plurality of points in the depth image.

Optionally, the act of determining the plurality of points in the reference image comprises: obtaining multiple depth images from different directions; processing the depth images to determine a three-dimensional surface model; determining a plurality of points from the three-dimensional surface model; and transferring the plurality of points from the three-dimensional surface model to a pixel domain of the reference image.

Optionally, the method further includes determining a displacement vector using one of the determined positions.

Optionally, the method further includes back projecting the displacement vector to a plane above a patient support supporting the patient.

Optionally, the method further includes determining a vertical displacement and a lateral displacement based on the back projected displacement vector.

Optionally, the input image comprises a camera image.

Optionally, the plurality of templates is generated using a x-ray image, a CT image, a CBCT image, a tomosynthesis image, a PET image, a SPECT image, an MRI image, a PET-CT image, or a SPECT-CT image.

Optionally, the positions are determined in substantially real-time to allow real-time monitoring of the patient.

Optionally, the method further includes generating a signal in response to at least one of the determined positions deviating from a reference position.

Optionally, the method further includes displaying graphics in a screen representing the determined positions.

Optionally, the act of determining the plurality of positions is performed during a radiation delivery.

Optionally, the radiation delivery comprises treatment radiation delivery.

Optionally, the radiation delivery comprises a delivery of imaging radiation.

An apparatus for monitoring a patient includes: a processing unit configured for: obtaining an input image having a plurality of regions of interest; and determining a plurality of positions for the respective plurality of regions of interest; wherein the processing unit is configured for determining the plurality of positions by: accessing a plurality of templates; comparing the plurality of templates with respective areas in the input image using a comparator in the processing unit; and determining the plurality of positions based at least in part on a result of the act of comparing.

Optionally, the processing unit is configured to perform the act of comparing by performing template matching using the input image and a plurality of templates for the respective regions of interest.

Optionally, the processing unit is configured to perform the act of comparing by performing a plurality of cross correlations between the areas in the input image and the plurality of templates.

Optionally, the processing unit is further configured for creating the plurality of templates, and wherein the apparatus further comprises a non-transitory medium for storing the templates.

Optionally, the processing unit is configured to perform the act of creating the plurality of templates by: obtaining a reference image; determining a plurality of points in the reference image; and generating the plurality of templates using pixels in the reference image, such that the templates have respective coordinates that correspond with respective positions of the determined points in the reference image.

Optionally, the processing unit is configured to perform the act of determining the plurality of points in the reference image by: determining a plane above a patient support supporting the patient; determining points on the plane; and transferring the plurality of points on the plane to a pixel domain of the reference image.

Optionally, the processing unit is configured to perform the act of determining the plurality of points in the reference image by: obtaining a depth image; processing the depth image to determine a plurality of points in the depth image; and transferring the plurality of points in the depth image to a pixel domain of the reference image.

Optionally, the processing unit is configured to perform the act of processing the depth image by thresholding depth values in the depth image so that pixels with depths corresponding to points within a virtual box surrounding the patient are included as candidates for the plurality of points in the depth image.

Optionally, the processing unit is configured to perform the act of determining the plurality of points in the reference image by: obtaining multiple depth images from different directions; processing the depth images to determine a three-dimensional surface model; determining a plurality of points from the three-dimensional surface model; and transferring the plurality of points from the three-dimensional surface model to a pixel domain of the reference image.

Optionally, the processing unit is further configured for determining a displacement vector using one of the determined positions.

Optionally, the processing unit is further configured for back projecting the displacement vector to a plane above a patient support supporting the patient.

Optionally, the processing unit is further configured for determining a vertical displacement and a lateral displacement based on the back projected displacement vector.

Optionally, the input image comprises a camera image.

Optionally, the plurality of templates is generated using a x-ray image, a CT image, a CBCT image, a tomosynthesis image, a PET image, a SPECT image, an MRI image, a PET-CT image, or a SPECT-CT image.

Optionally, the processing unit is configured to determine the positions in substantially real-time to allow real-time monitoring of the patient.

Optionally, the processing unit is further configured for generating a signal in response to at least one of the determined positions deviating from a reference position.

Optionally, the apparatus further includes a screen for displaying graphics representing the determined positions.

Optionally, the processing unit is a part of, or an accessory for, a radiation delivery system.

Optionally, the radiation delivery system comprises a treatment radiation delivery system.

Optionally, the radiation delivery system comprises a imaging radiation delivery system.

Optionally, the apparatus further includes a first optical camera and a second optical camera communicatively coupled to the processing unit A product includes a non-transitory medium storing a set of instructions, an execution of which by a processing unit causes a method for monitoring a patient in a medical procedure to be performed, the method comprising: obtaining an input image having a plurality of regions of interest; and determining a plurality of positions for the respective plurality of regions of interest; wherein the act of determining the plurality of positions comprises: accessing a plurality of templates; comparing the plurality of templates with respective areas in the input image; and determining the plurality of positions based at least in part on a result of the act of comparing.

Other and further aspects, features, details, and embodiments will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
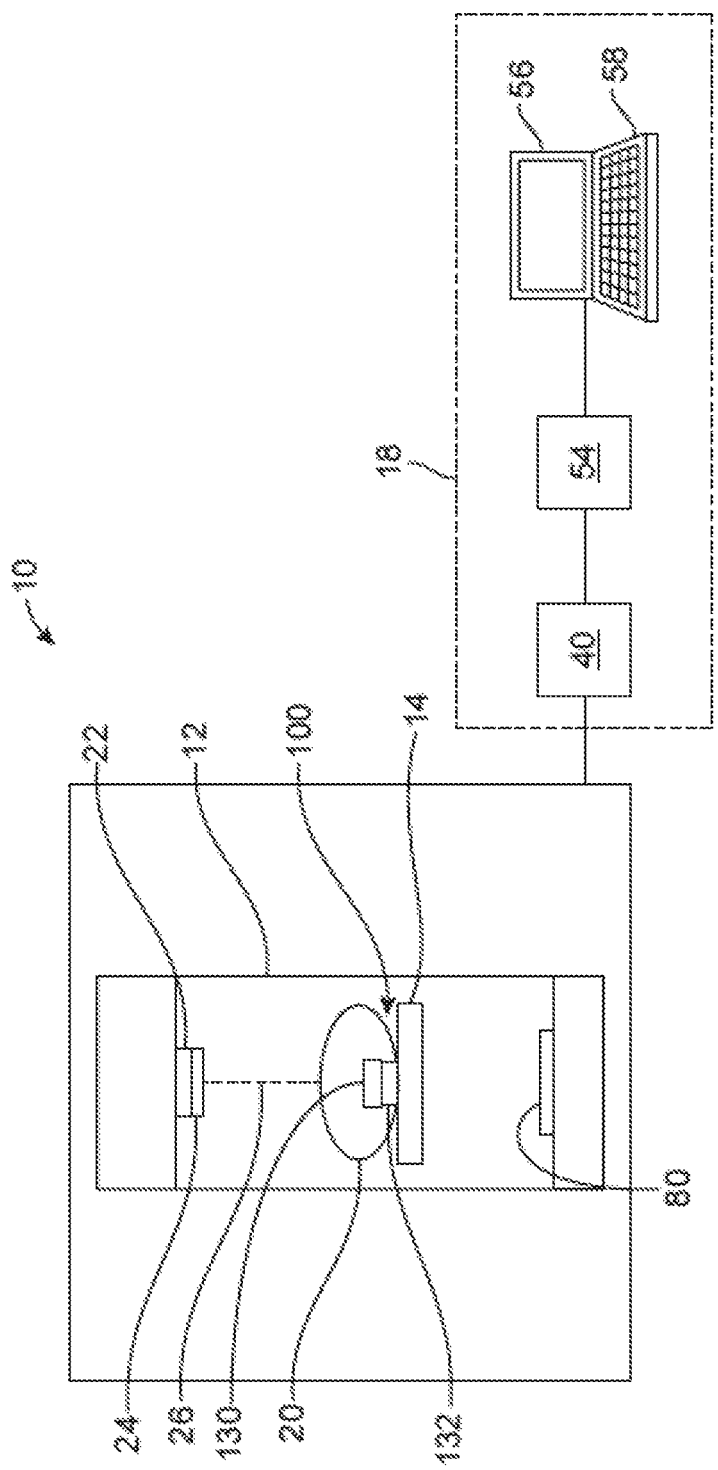
FIG. 1 illustrates a radiation treatment system having a patient monitoring system in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Radiation Systems

FIG. 1 illustrates a radiation treatment system 10. The system 10 includes an arm gantry 12, a patient support 14 for supporting a patient 20, and a control system 18 for controlling an operation of the gantry 12 and delivery of radiation. The system 10 also includes a radiation source 22 that projects a beam 26 of radiation towards the patient 20 while the patient 20 is supported on support 14, and a collimator system 24 for changing a cross sectional shape of the radiation beam 26. The radiation source 22 may be configured to generate a cone beam, a fan beam, or other types of radiation beams in different embodiments. Also, in other embodiments, the source 22 may be configured to generate proton beam as a form of radiation for treatment purpose. Also, in other embodiments, the system 10 may have other form and/or configuration. For example, in other embodiments, instead of an arm gantry 12, the system 10 may have a ring gantry 12.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purpose. In such cases, the system 10 will include an imager, such as the imager 80, located at an operative position relative to the source 22 (e.g., under the support 14). In further embodiments, the radiation source 22 may be a treatment radiation source for providing treatment energy, wherein the treatment energy may be used to obtain images. In such cases, in order to obtain imaging using treatment energies, the imager 80 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 22 is able to generate X-ray radiation at a plurality of photon energy levels within a range anywhere between approximately 10 keV and approximately 20 MeV. In further embodiments, the radiation source 22 can be a diagnostic radiation source. In such cases, the system 10 may be a diagnostic system with one or more moving parts. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing unit 54, such as a processor, coupled to a control 40. The control system 18 may also include a monitor 56 for displaying data and an input device 58, such as a keyboard or a mouse, for inputting data. The operation of the radiation source 22 and the gantry 12 are controlled by the control 40, which provides power and timing signals to the radiation source 22, and controls a rotational speed and position of the gantry 12, based on signals received from the processing unit 54. Although the control 40 is shown as a separate component from the gantry 12 and the processing unit 54, in alternative embodiments, the control 40 can be a part of the gantry 12 or the processing unit 54.

In some embodiments, the system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an IMRT procedure).

In other embodiments, the system 10 may not be a treatment radiation system. Instead, the system 10 may be a diagnostic radiation system. In such cases, the radiation source 22 is a diagnostic radiation source configured to provide radiation with energy suitable for imaging purposes.

Patient Monitoring

Figure 2:
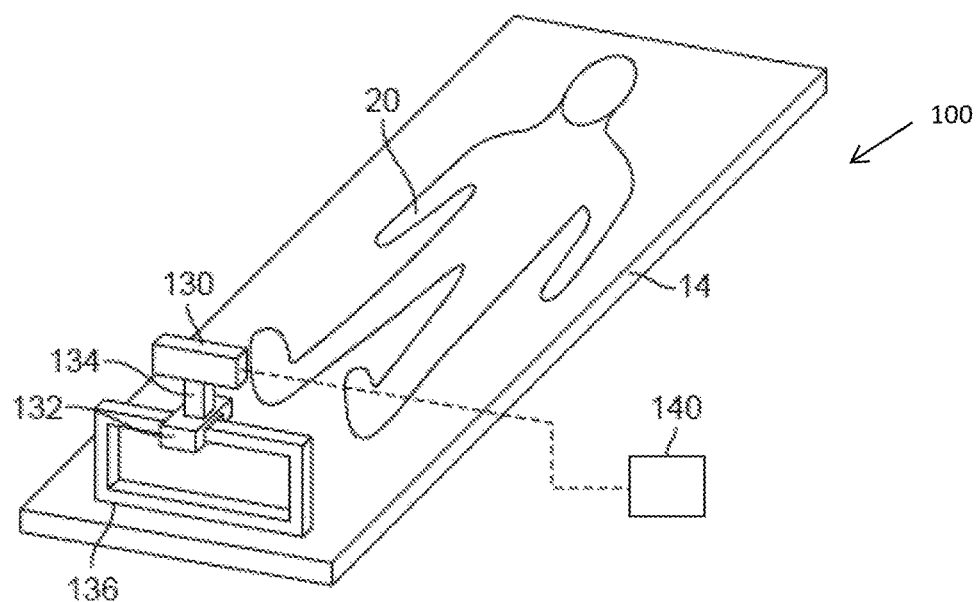
FIG. 2 illustrates a patient monitoring system.

As shown in FIGS. 1 and 2, the radiation system 10 also includes a patient monitoring system 100. In some embodiments, the patient monitoring system 100 may be considered to be a part of the radiation system 10. In other embodiments, the patient monitoring system 100 may be an accessory for the radiation system 10.

The patient monitoring system 100 is configured to monitor positions of the various parts of the patient during an operation being performed by the radiation system 10. The patient monitoring system 100 includes a camera 130, a securing mechanism 132, a support 134, and a processing unit 140. The camera 130 is configured to capture images of the patient being monitored.

The support 134 may be a post, a bracket, a beam, an arm, etc., for supporting the camera 130. The securing mechanism 132 may be located at the support 134. Also, in some embodiments, the support 134 may optionally have one or more moveable parts to allow a position and/or an orientation of the camera 130 to be adjusted relative to the support 14 (or relative to the patient 20 or another reference location). In some embodiments, the support 134 itself may be movable relative to the support 14 in order to adjust the camera position (e.g., longitudinally) relative to the patient. In further embodiments, the support 134 may be a base with a tilt motor, which allows the camera 130 to be tilted in one, two, or three, degrees of movement relative to the base. In other embodiments, the support 134 is not needed, and the patient monitoring system 100 may not include the support 134.

Figure 3:
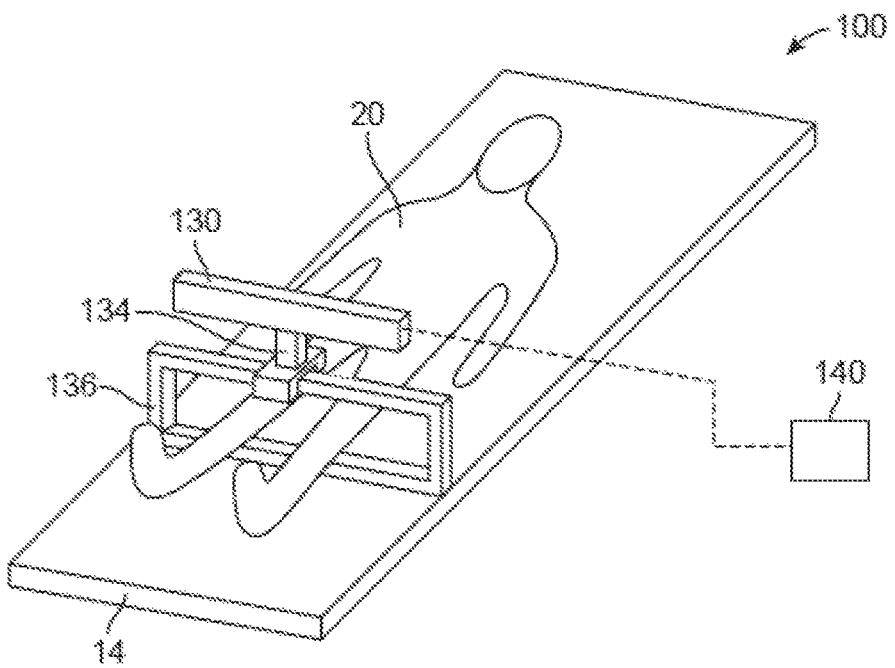
FIG. 3 illustrates another patient monitoring system.

In the illustrated embodiments, the securing mechanism 132 is configured to secure the camera 130 to a bracket 136 at the foot of the support 14. The bracket 136 may be considered as a part of the patient monitoring system 100 in some embodiments. Alternatively, the bracket 136 may be considered as a part of the patient support 14. In some embodiments, the bracket 136 may have an opening to allow the patient's feet to go through it if necessary (FIG. 3). For example, the bracket 136 may have an opening height that is more than 8 inches, such as 10 inches, 12 inches, 14 inches, etc., in order to allow the patient's feet to enter therethrough.

In other embodiments, the bracket 136 is optional, and the securing mechanism 132 may be configured to secure the camera 130 directly to the patient support 14, or to other component(s) of the medical system 10. In further embodiments, the securing mechanism 132 may be configured to secure the camera 130 to a room, such as to a ceiling, a wall, or a floor. In still further embodiments, the securing mechanism 132 may be configured to secure the camera 132 to a structure that is not a part of the medical system 10. The securing mechanism 132 may be a clamp for grasping an object, a screw for insertion into a screw slot located in an object to which the camera 130 is to be secured against, a snap-and-fit type connector, a hook-and-loop type connector, or any of other types of securing mechanism. In still further embodiments, the securing mechanism 132 is not required, and the patient monitoring system 100 does not include the securing mechanism 132. For example, in other embodiments, the support 134 may be a base, and the base may be placed on a flat surface that supports the camera 130 during use.

In the illustrated embodiments, the camera 130 is mounted above the top surface of the support 14. The height of the camera 130 may be adjustable so that the head of the patient 20 is visible over his/her belly. Also, the orientation of the camera 130 may be adjustable to adjust a viewing angle (e.g., relative to a horizontal surface). It should be noted that mounting the camera 130 so that its position is fixed relative to the support 14 is advantageous because such configuration allows the camera 130 to move with the patient support 14 (and therefore the patient 20) irrespective of the movement of the support 14.

The processing unit 140 is communicatively coupled to the camera 130.

The processing unit 140 is configured to process signals transmitted from the camera 130, and to determine whether there is patient movement based on the signals. The processing unit 140 may communicate with the camera 130 using a wire, or using a wireless device. In some embodiments, the processing unit 140 may be a processor, such as an ASIC processor, a FPGA processor, a general purpose processor, or any of other types of processor. Also, the processing unit 140 may include hardware, software, or combination of both. Also, in some embodiments, the processing unit 140 may be the same as the processing unit 54, or a component of the processing unit 54. In other embodiments, the processing unit 140 may be considered to be a part of the radiation system 10, and not a part of the patient monitoring system 100.

Figure 4:
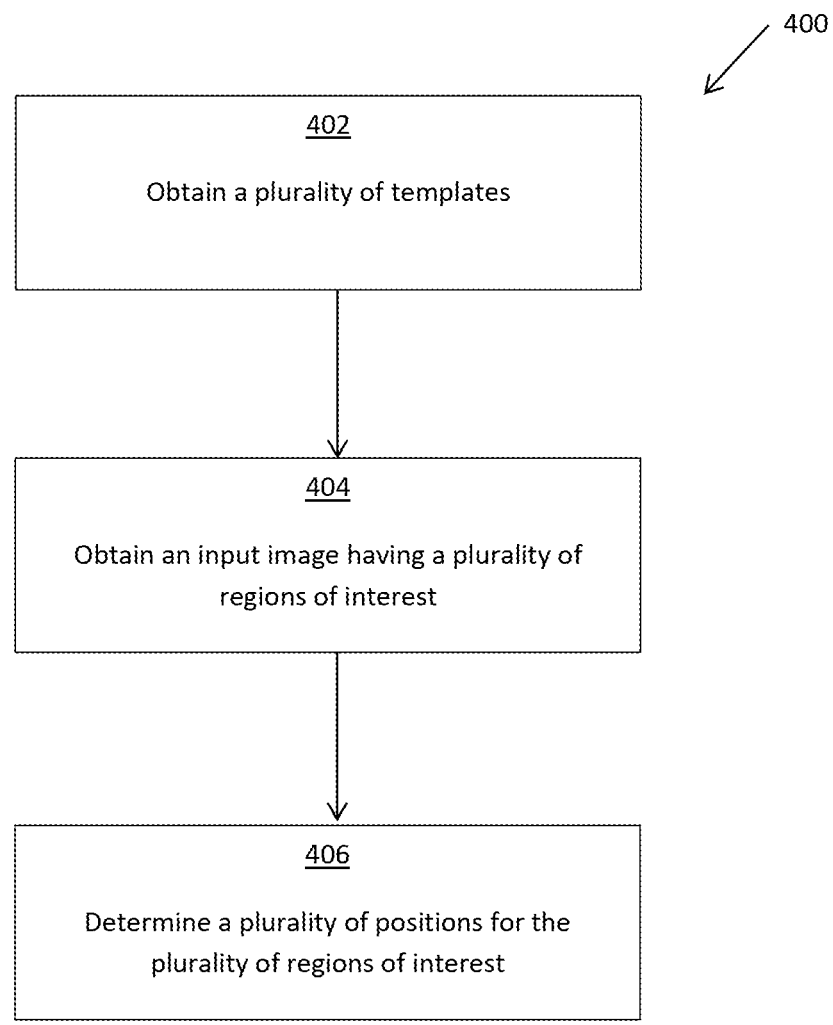
FIG. 4 illustrates a method for monitoring a patient in accordance with some embodiments.

FIG. 4 illustrates a method 400 of monitoring a patient in accordance with some embodiments. The method 400 will be described as being performed using the patient monitoring system 100. Also, the method 400 will be described with reference to monitoring the patient during a medical procedure being performed by the radiation system 10 of FIG. 1. However, it should be noted that the method 400 may be performed to monitor a patient during other types of medical procedures, which may or may not involve use of radiation.

Before performing the method 400, the patient is set up and is supported on the patient support 14 of the radiation system 10. After the patient is supported, a plurality of templates is obtained (item 402).

In some embodiments, the templates were already previously created, e.g., in a previous session (which may occur on the same day or different day for the method 400), or in the same session as that for the method 400. In such cases, the act of obtaining the templates may be performed by the processing unit 140 retrieving the templates from a non-transitory medium that stores the templates. Alternatively, the act of obtaining the templates may be performed by the processing unit 140 accessing the non-transitory medium storing the templates.

In other embodiments, the act of obtaining the templates may involve generation of the templates. In such cases, the generation of the templates may be performed by the camera 130 capturing a reference image of the patient. Then the processing unit 140 processes the reference image to create the set of templates.

Figure 5:
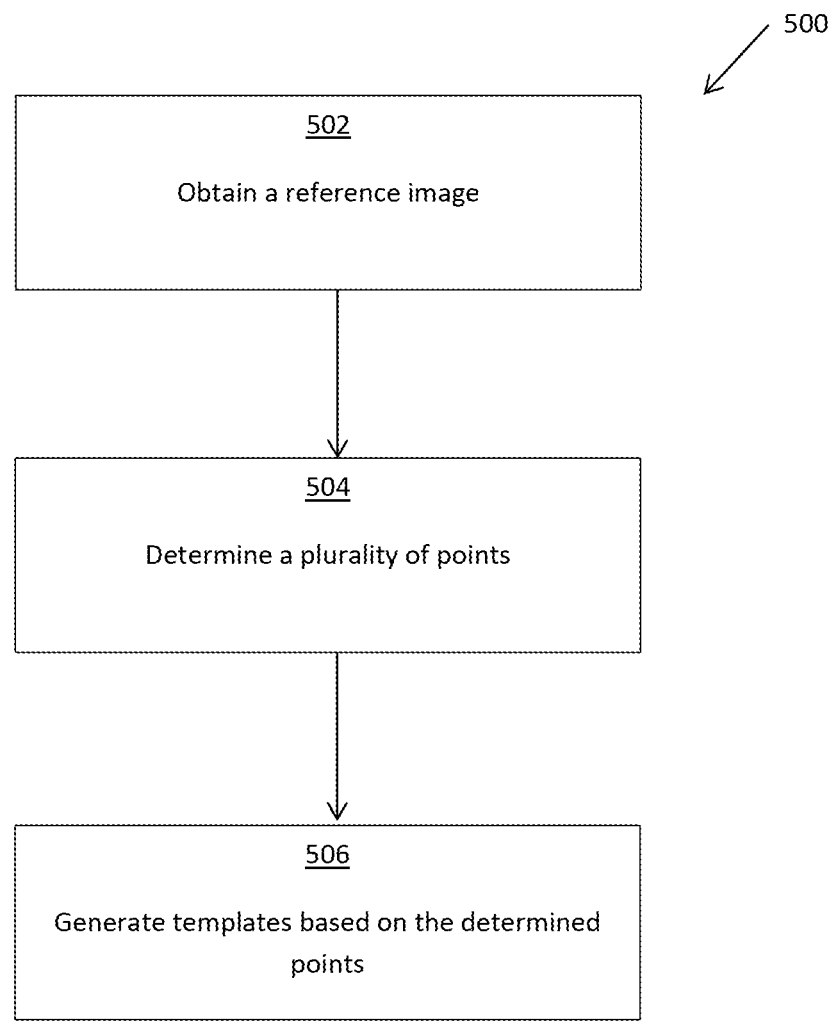
FIG. 5 illustrates a method for generating templates for patient monitoring in accordance with some embodiments.

FIG. 5 illustrates a method 500 of creating a plurality of templates in accordance with some embodiments. First, a reference image is obtained (item 502). This may be accomplished by the processing unit 140 receiving the reference image from the camera 130. Alternatively, item 502 may be accomplished by the camera 130 generating the reference image, and transmitting the reference image for reception by the processing unit 140. Next, a plurality of points (monitoring points) is determined (item 504). The points are determined with respect to the coordinate frame of the reference image. Next, the templates are generated using pixels in the reference image based on the determined points (item 506). In some embodiments, the templates are generated such that the templates have respective coordinates (in the coordinate frame of the reference image) that correspond with respective positions of the determined points with respect to the reference image.

Figure 6:
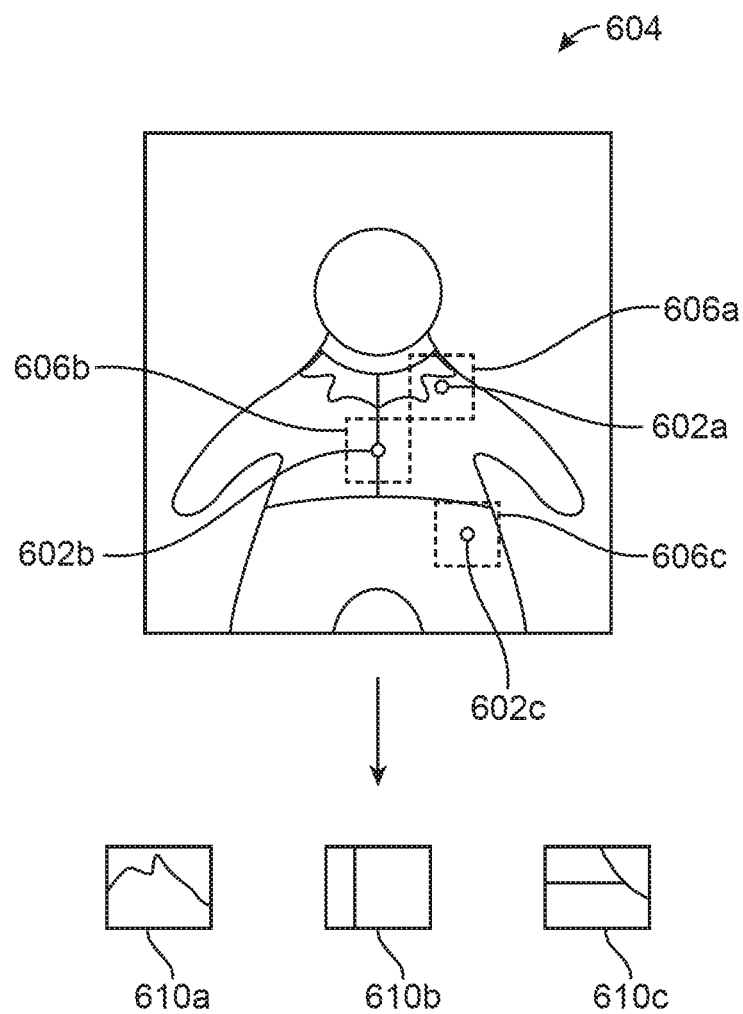
FIG. 6 illustrates an example of templates being generated from a reference image.

FIG. 6 illustrates graphically the concept of items 504 and 506. As shown in FIG. 6, various points 602a-602c in the reference image 604 corresponding to respective regions of interest 606a-606c are shown. Once the points 602a-602c in the coordinate frame of the reference image 604 have been determined, a plurality of templates 610a-610c may be generated using pixels from the reference image 604, such that the templates 610a-610c have respective template positions that correspond with the positions of the points 602a-602c. In the illustrated embodiments, each template 610 is a rectangular region constituting a subset of the reference image 604 that centers at a respective point 602. In other embodiments, the templates 610 may be created so that they correspond with the positions of the respective points 602. For example, corners or edges of the respective templates 610 may be aligned with respective points 602. Also, in other embodiments, each template 610 may have a shape that is different from a rectangle (e.g., a template may have a square shape, a triangular shape, a circular shape, an oval shape, or a customized shape). The customized shape may be one that conforms to a specific body part (such as the face or upper torso, or arm, etc.) as seen in the image. Furthermore, in some embodiments, a template may have an irregular shape. In addition, in the illustrated embodiments, the templates 610 have the same shape and size. In other embodiments, two or more of the templates 610 may have different shapes and/or sizes. Furthermore, in some embodiments two or more of the templates 610 may have overlapping region(s). In other embodiments, the templates 610 may not overlap. Although only three templates 610a-610c are shown in the example, in other embodiments, there may be fewer than three templates (e.g., two templates), or more than three templates.

After the templates have been generated, the templates may then be stored in a non-transitory medium for later use.

Figure 7:
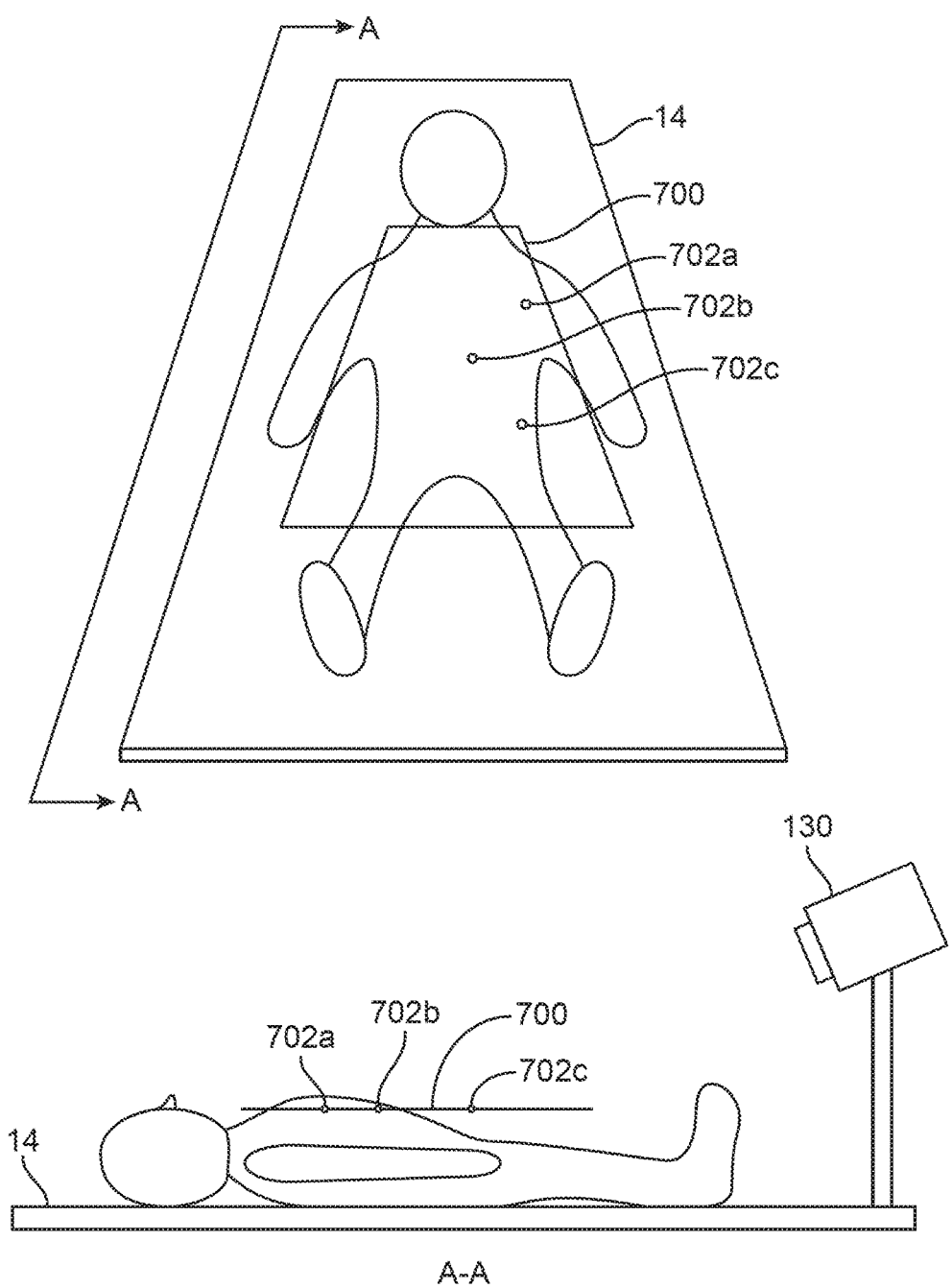
FIG. 7 illustrates a technique for designating points for template generation.

Various techniques may be employed to determine the points with respect to the coordinate frame of the reference image for generating the templates. In some embodiments, a graphical user interface may be provided for allowing a user to manually designate certain points in the coordinate frame of the reference image for generating the templates. In other embodiments, as shown in FIG. 7, the plurality of points in the coordinate frame of the reference image may be determined by: determining a plane 700 above the patient support 14 supporting the patient; determining points 702a-702c on the plane 700; and transferring the plurality of points on the plane 700 to a pixel domain of the reference image. As shown in FIG. 7, in some embodiments, the plane 700 above the patient support 14 may be a horizontal plane, or may be a plane forming an angle with respect to the surface of the patient support 14, or a plane that approximates the patient body contour over a specified area such as patient chest. In one implementation, the camera pixel resolution (radians per pixel) plus its orientation angles and position relative to the patient support 14 may be calibrated. Then the patient surface may be approximated as a plane 700 that is parallel to the surface of the patient support 14, and that is positioned at a height equal to patient thickness above it. This allows a user to manually designate, or the processing unit 140 to automatically designate, points 702 on this plane 700 that are near the treatment target position. Using the position and orientation of the camera 130 with respect to the plane 700 (or the points 702 on the plane 700), the processing unit 140 then forward projects these monitoring points 702 to the optical camera 130 pixel domain (e.g., the reference image). From the reference image, one template for each forward projected pixel position is determined (e.g., the template may be centered on the forward projected pixel) and saved in a non-transitory medium. It should be noted that the position (e.g. height) of the plane 700 may be selected based on a thickness or the patient. For example, the bigger the patient, the higher the height from the patient support 14 may be selected.

Figure 8:
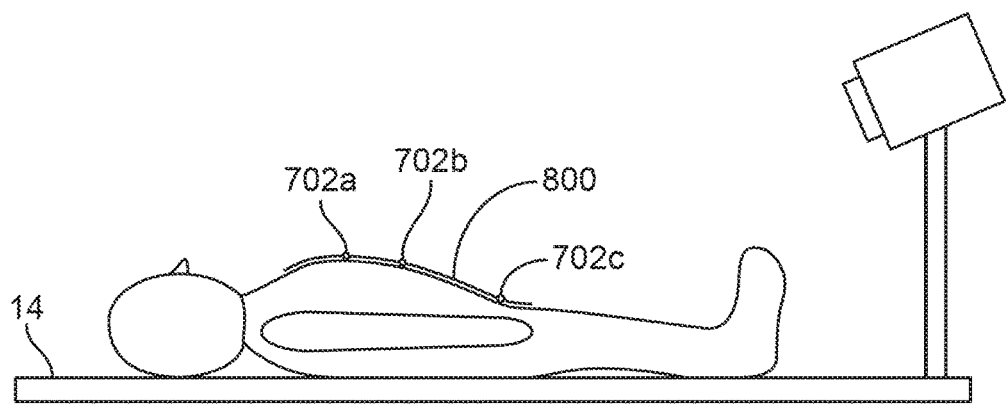
FIG. 8 illustrates another technique for designating points for template generation.

In some embodiments, the generating of the templates is achieved using one or more cameras that image the actual surface of the patient. In other embodiments, a depth sensing camera may be employed to assist in the determination of points in the coordinate frame of the reference image for generating the templates. In one implementation, the act of determining the plurality of points in the reference image comprises: obtaining a depth image; processing the depth image to determine a plurality of points in the depth image; and transferring the plurality of points in the depth image to a pixel domain of the reference image. Optionally, the act of processing the depth image may comprise thresholding depth values in the depth image so that pixels with depths corresponding to points within a virtual box surrounding the patient are included as candidates for the plurality of points in the depth image. In some embodiments, the processing unit 140 may use the depth image to create a 3D surface map (curvilinear plane) 800 of the scene imaged by the camera (FIG. 8). This is then used to segment (isolate) the patient from other objects surrounding it, for example by excluding all 3D points outside a virtual box that is centered relative to the patient support 14. Thus, use of a depth image may allow designation of the monitoring points 702a-702c on the 3D patient surface 800 without the planar approximation mentioned above. Also by automatic segmentation of patient body parts, e.g. arms vs. torso, the monitoring points can be placed on specific anatomic parts of the patient. After the points 702 from the 3D surface 800 have been designated, the points may be forward projected to the optical camera pixel domain using a transformation between the depth camera and the optical camera. Embodiments with depth sensing camera will be described in further detail below.

In some embodiments, the templates may be obtained when a breathing of a patient is at a peak of the inhale phase. In other embodiments, the templates may be obtained when a breathing of the patient is at an exhale phase. In other embodiments, the templates may be obtained at any desired breathing phase. In one implementation, the patient monitoring system 100 may acquire templates at any starting time, and as soon as the exhale-end, or another desired phase, of a breathing motion is reached, the patient monitoring system 100 may then acquire a new set of templates. In some cases, the detection of the desired phase of a breathing motion may be detected by processing the motion signal corresponding to the initial template, because a template acquired at an arbitrary point in breathing cycle still generates a breathing signal from which the exhale and inhale ends can be detected.

Returning to FIG. 4, after the templates have been obtained in item 402, then an input image having a plurality of regions of interest is obtained (item 404). In some embodiments, the act of obtaining the input image may be performed by the processing unit 140 receiving a camera image (image signals) from the camera 130. The camera image may be a real-time video image from a sequence of video images generated by the camera 130. In other embodiments, the act of obtaining the input image may be performed by the camera 130 capturing an image of the patient, and transmitting the image to the processing unit 140 for reception by the processing unit 140.

Next, the processing unit 140 determines a plurality of positions for the respective plurality of regions of interest (item 406). In the illustrated embodiments, the act of determining the plurality of positions includes: accessing a plurality of templates from the non-transitory medium storing the templates; comparing the plurality of templates with respective areas in the input image; and determining the plurality of positions based at least in part on a result of the act of comparing. In one implementation, the processing unit 140 may include a position determination module configured to access the templates. The position determination module may include a comparator configured to compare the templates with respective areas in the input image. In some embodiments, the act of comparing may include performing template matching using the input image and a plurality of templates for the respective regions of interest. In other embodiments, the act of comparing may include performing cross correlations (e.g., normalized cross correlations) between the areas in the input image and the plurality of templates. The determined positions are for the respective monitoring points (that corresponds to the different respective regions of interest in the real-time input image). The position determination module may include an output for outputting the determined positions. In some embodiments, the comparator in the position determination module may be configured to process different parts of the input image with respect to the templates sequentially, but doing so in a sufficient speed so that the positions may be determined by the processing unit 140 in substantially real time. In other embodiments, the comparator in the position determination module may be configured to process different parts of the input image with respect to the templates in parallel, and doing so in a sufficient speed so that the positions may be determined by the processing unit 140 in substantially real time.

Figure 9:
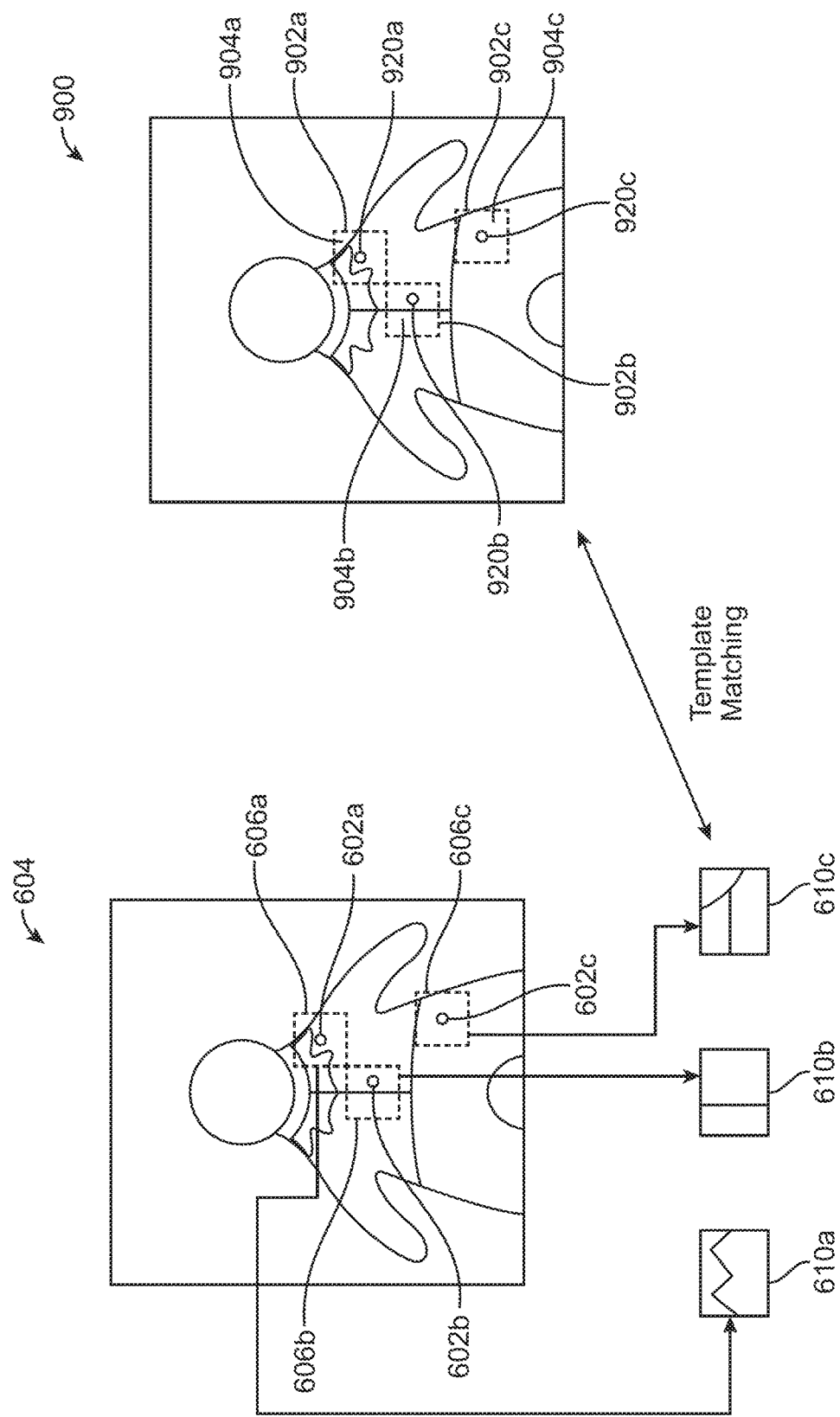
FIG. 9 illustrates a plurality of positions being determined for respective regions of interest.

An example of the concept of item 406 is shown in FIG. 9. As shown in the figure, an input image 900 is processed by the processing unit 140 to identify the matching regions of interest 902a-902c. Such may be accomplished by the processing unit 140 performing template matching between different search areas 904a-904c in the input image with the respective templates 610a-610c. The identified matching regions of interest 902a-902c have respective positions (X, Y) that are determined based on an identification of the regions of interest 902a-902c (e.g., a matching between the areas 904a-904c and the templates 610a-610c, respectively). In the example, the three determined positions are represented as three points 920a-920c overlay in the input image 900. In some embodiments, the points 920a-920c may be centered in the respective identified regions of interest in the input image, and may represent the real-time positions of the respective regions of interest. The three points 920a-920c have positions $(X1_0, Y1_0)$, $(X2_0, Y2_0)$, and $(X3_0, Y3_0)$. Thus, the template matching technique allows the monitoring points corresponding to different parts of the patient to be determined and tracked in real-time during the medical procedure. During item 406, the processing unit 140 may be configured to search for matching areas with the templates 610 in the current input image 900 using the previously identified points 920 from the last input image as estimates. The three determined positions $(X1, Y1)$, $(X2, Y2)$, $(X3, Y3)$ for the three matched areas (regions of interest 902a-902c) may be stored in a non-transitory medium. Alternatively, or additionally, the determined positions may be presented on a screen (e.g., in a form of numbers or graphics) for viewing by a user. Also, in some embodiments, graphics like that shown in FIG. 9 may also be displayed in the screen for viewing by the user.

It should be noted that using image camera to monitor actual regions on the patient is advantageous over the technique that generates a "relief map" on a patient surface. Structured light may be used for surface relief mapping. For example, structured light reflected from a surface may be used for surface relief mapping. Time-of-flight and laser scanning (a form of structured light) are other possible methods. In one technique, a pattern (e.g., a random pattern of dots, a pre-determined pattern of dots, etc.) may be projected using structure light on a patient's surface. Two or more stereo cameras that are sensitive to the color of this pattern are then used to image the surface. Then template matching is performed using the images from the camera, and stereo triangulation is performed to determine a 3D point solution. However, imaging the relief map on the patient may not be as desirable as imaging the actual surface (e.g., patient's skin, gown, cloth, blanket, etc.) of the patient. This is because an optical image of the patient (e.g., patient's skin, gown, cloth, blanket, etc.) contains rich texture that is viewable. The above method provides very high sensitivity and accuracy because the imaged texture has much more spatial information than a relief map. For example, surface relief of a typical torso even including a woman's breast does not nearly have the same amount of spatial information that a patch of hospital gown has. This has major consequence on the performance of any matching algorithm (e.g., matching algorithm that uses cross-correlation).

In some embodiments, after the positions are determined in item 406, the determined positions may be transformed from the coordinate frame of the image to a coordinate frame associated with the radiation system 10. This allows the various positions of the monitoring points to be expressed relative to the radiation system 10. In one implementation, the processing unit 140 may include a position transformation module having an input for receiving the determined positions, and an output for outputting transformed positions in a coordinate frame that is associated with the radiation system 10. The position transformation module may be configured to compute the transformed positions using a position transformation algorithm that uses the determined positions as input.

Also, in some embodiments, after the positions are determined, the method 400 may further include determining one or more displacement vectors using one or more of the determined positions, respectively. The displacement vector may be calculated as a difference between the determined position and a reference position. The reference position may be the a point 602 as overlayed on the input image. Following the above example, the displacement vectors for the three regions of interest 902 may be calculated as $(X1-X1_0, Y1-Y1_0)$, $(X2-X2_0, Y2-Y2_0)$, and $(X3-X3_0, Y3-Y3_0)$. The displacement vectors may be stored in a non-transitory medium. Alternatively, or additionally, the displacement vectors may be presented on a screen (e.g., in a form of numbers or graphics) for viewing by a user. In some cases, the processing unit 140 may include a displacement vector determination module for calculating the displacement vectors.

In other embodiments, if the patient monitoring system 100 has a depth sensing feature (e.g., a separate depth sensing camera, or a depth sensing device integrated with the optical image camera 130), then a real-time depth image may be obtained to determine the displacements. In one implementation, a set of templates, each of which having a patch of a 3D surface map, may be generated and obtained by the processing unit 140. Then during patient monitoring, the processing unit 140 may determine the positions and displacements of certain points (the monitoring points) on the 3D surface map (generated from a real-time input depth image) by template matching using the templates.

Figure 10:
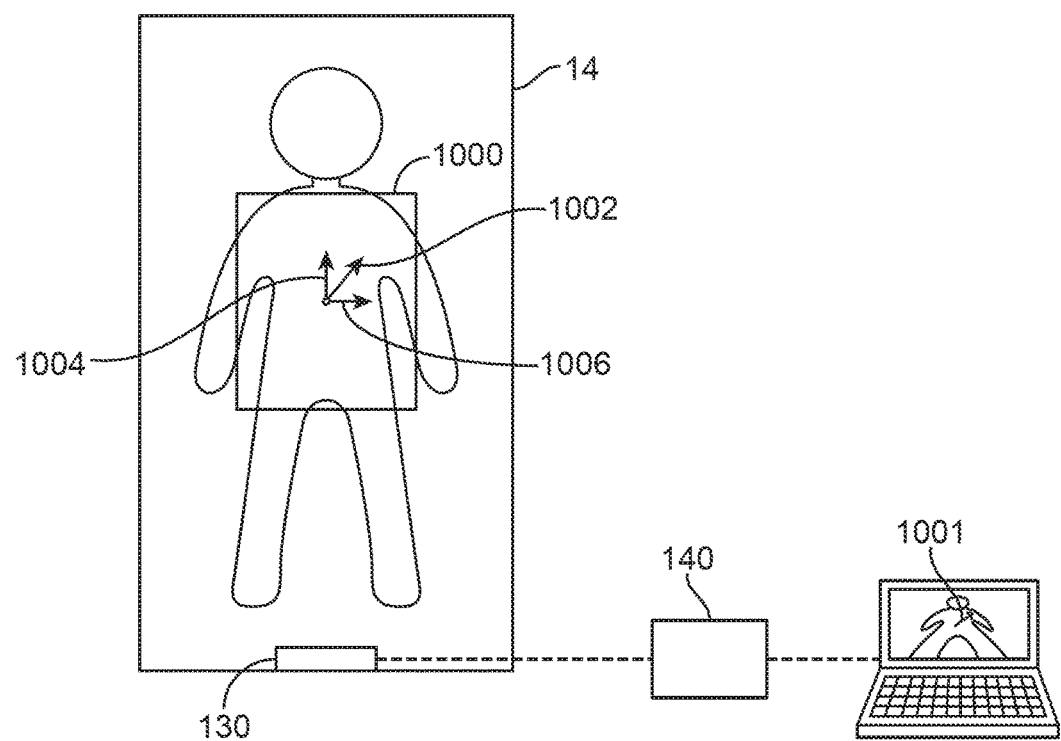
FIG. 10 illustrates projecting displacement vector onto a plane.

It should be noted that the displacement vectors described previously are in the coordinate frame of the input image. In some embodiments, the method 400 may further include projecting (e.g., transforming) the displacement vectors to another coordinate frame. For example, in some embodiments, the displacement vectors may be projected by the processing unit 140 to a plane that is above the patient support supporting 140 the patient. For example, as shown in FIG. 10, the plane 1000 may be a horizontal plane (for approximating the patient surface) that is parallel to a surface of the patient support 140 supporting the patient. The plane 1000 may be the same plane 700 as the one used for estimating the patient surface for designation of monitoring points. In other embodiments, the plane 1000 may be any arbitrary plane (which may or may not be horizontal). For example, in other embodiments, the plane may be non-parallel, and may form a non-zero angle with respect to the surface of the patient support 140.

It should be noted that the two dimensional (2D) pixel domain displacement vector may be back projected to any plane defined relative to the machine-based coordinates, thus producing two estimated motion components that may be interpreted, for example, relative to the radiation beam. Thus, this plane to which the 2D pixel domain displacement vector is back projected may be any arbitrary plane set by a user. For smaller camera look-down angles, a vertical plane may be more desirable (but the plane may be non-vertical in other embodiments). For larger look-down angles (e.g., a camera looking almost straight down at the patient), a horizontal plane may be more desirable (but the plane may be non-horizontal in other embodiments). In one implementation, the processing module 140 may include a back projection module to perform the above functions. The back projection module takes the 2D displacement vector as input, and performs a back projection calculation to project the vector to a defined plane. In some embodiments, if the patient monitoring system 100 includes a depth sensing camera for providing an associated depth image, then the plane tangent to the patient surface at the reference point may be desirable for the back projection. If the depth image is higher precision (such as that obtained using a time-offlight depth camera), then the pixel-domain 2D vector may be back projected to the patient surface, which is not necessarily planar, thus producing a real 3D displacement vector not limited to be in a plane.

In some embodiments, the projection of a displacement vector 1001 (in the coordinate frame of the input image) to the plane 1000 (e.g, the plane 700 approximating the patient surface) may be performed using the distance between the camera 130 and the monitored point on the plane/patient surface, and an orientation of the camera 130. In some embodiments, if the patient monitoring system 100 includes a depth sensing camera for providing a depth image, the pixel-domain displacement vector can be converted more precisely from the pixel-domain (i.e., the coordinate of the input image) to a coordinate associated with the patient by back projecting the displacement vector to the actual 3D reference point on the patient (i.e., the point on the 3D surface generated from the depth image) as opposed to the point on an approximating plane (which is the case if no depth sensing camera is provided). As shown in FIG. 10, optionally, for each projected displacement vector 1002, the method may further include determining a vertical displacement 1004 and a lateral displacement 1006 based on the projected displacement vector 1002. Such may be performed by the processing unit 140. The projected displacement vectors 1002 and/or the corresponding vertical and lateral displacements 1004, 1006 may be stored in a non-transitory medium. Alternatively, or additionally, they may be presented on a screen (e.g., in a form of numbers or graphics) for viewing by a user.

In other embodiments, if the patient monitoring system 100 has a depth sensing feature (e.g., a separate depth sensing camera, or a depth sensing device integrated with the optical image camera 130), then a real-time depth image may be obtained to allow a more precise projection/conversion of the pixel domain displacement (e.g., from the coordinate frame of the image to the coordinate frame associated with the patient). For example, in some embodiments, a real-time depth image may be provided from the depth sensing device to the processing unit 140 for 3D surface generation. The 3D surface may then be used by the processing unit 140 to calculate the actual distances between the camera 130 and the respective monitoring points on the patient. The processing unit 140 may then use the actual distances to calculate the projected displacement vectors.

Also, in some embodiments, the patient monitoring system 100 may optionally further include a screen for displaying information. In such cases, the method 400 may optionally further include displaying graphics in a screen representing the determined positions (X, Y), the reference positions (X0, Y0), displacement vectors, projected displacement vectors, vertical and horizontal displacements of the respective projected displacement vectors, or any combination of the foregoing.

In some embodiments, the processing unit 140 may generate a signal in response to at least one of the determined positions deviating from a reference position. In such case, the method 400 may optionally further includes generating a signal in response to a determined position deviating from a reference position. For example, if the processing unit 140 determines that a displacement vector or a projected displacement vector has a non-zero value, or has a value that exceeds a prescribed maximum threshold, then the processing unit 140 may generate a signal. The signal may cause a graphical signal to be presented on a screen for viewing by the user. Alternatively, or additionally, the signal may activate an alarm and/or stop an operation of the radiation system 10.

In addition, or in the alternative, in some embodiments, the processing unit 140 may be configured to analyze a pattern of the positions for a certain monitoring point. For example, one of the monitoring points may be at a patient's chest, and therefore it may correspond with a breathing of the patient. In such cases, the processing unit 140 may monitor the breathing pattern of the patient by considering the determined positions of the monitoring point that were determined within a prescribed period (e.g., within the last 15 seconds). If the patient's breathing becomes non-periodic or irregular, then the processing unit 140 may stop the operation of the radiation system 10.

In further embodiments, the determined positions at the various monitoring points may be used by the processing unit 140 to gate an operation of the radiation system 10. For example, the processing unit 140 may be configured to control the radiation system 10 to deliver radiation if a determined position for one of the monitoring points is within an amplitude range, and/or to stop delivery of radiation if the determined position is outside an amplitude range.

In still further embodiments, the determined positions may be used by the processing unit 140 to determine a phase of a respiratory cycle for the patient. For example, the processing unit 140 may include a phase determination module to perform such function. The phase of a respiratory cycle represents a degree of completeness of the breathing cycle. In some embodiments, the phase of a respiratory cycle may range from 0° to 360°, wherein phase=0° represents a beginning of a breathing cycle, and phase=360° represents an end of a breathing cycle. The determined phase may be used by the processing unit 140 to gate an operation of the radiation system 10. For example, the processing unit 140 may be configured to control the radiation system 10 to deliver radiation if a determined phase satisfies a phase requirement (e.g., is within a prescribed phase range), and/or to stop delivery of radiation if the determined phase fails the phase requirement (e.g., is outside a prescribed phase range). In one implementation, the processing unit 140 may include a control signal generation module that includes an input for receiving a determined phase of a respiratory cycle. The control signal generation module may also include a phase analysis module for analyzing the determined phase to determine whether it satisfies a requirement (e.g., outside a defined phase range, inside a defined phase range, meeting a phase value, etc.). If the requirement is satisfied, the control signal generation module then outputs a control signal to control a component of a radiation system.

Also, in some embodiments, the items in method 400 may be repeated as the medical procedure is continued to be performed by the radiation system 10. Thus, the processing unit 140 processes the real-time images at different times to continuously monitor the patient positions.

It should be noted that the above technique for patient monitoring may be performed during a radiation delivery. Thus, the act of determining the plurality of positions in the method 400 may be performed during a radiation delivery. In some embodiments, the radiation delivery comprises treatment radiation delivery. In other embodiments, the radiation delivery comprises a delivery of imaging radiation. In other embodiments, the method 400 may be performed during other medical procedures that may not involve use of radiation. Also, in some embodiments, the reference image and the templates may be obtained immediately after the patient is set up for a medical procedure. The medical procedure may be one that requires the patient not to move, such as CBCT acquisition prior to treatment, or radiation dose delivery during treatment. In other embodiments, the medical procedure may be one that requires the patient to move (e.g., to breath in a certain pattern).

In some embodiments, the method 400 may be performed in substantially real time to allow real-time monitoring of the patient, while a medical procedure is being performed on the patient (e.g., while the radiation system 10 delivers radiation to the patient). Thus, the positions of the respective regions of interest in the real-time input image may be determined in substantially real-time in some embodiments. As used in this specification, the term "substantially real time" or "real time" refers to an item that occurs shortly (e.g., within 1 second, and preferably within 0.5 second, and more preferably within 0.1 second) after an event. For example, a "real time" input image may be an image that is obtained by the processing unit 140 shortly after the image is generated. As another example, a position that is determined in "substantially real time" may be a position that is determined shortly after an input image capturing the position is generated. In other embodiments, the method 400 may not be performed in substantially real time. For example, in other embodiments, a sequence of input images may be generated and recorded for later processing by the processing unit 140.

It should be noted that the patient monitoring system 100 is advantageous because it allows monitoring of multiple points associated with the patient simultaneously. In some embodiments, different points may be monitored with respect to different monitoring criteria. For example, there may be one monitoring point on a patient's chest, and another monitoring point on the patient's arm. During a treatment procedure performed by the system 10, the processing unit 140 may monitor the "chest" point to make sure that the patient's is breathing according to a desired breathing pattern. At the same time, the processing unit 140 may also simultaneously monitor the "arm" point to make sure that the patient's arm stays stationary, or does not move excessively (i.e., beyond a prescribed threshold) during the treatment procedure. Thus, different monitoring criteria may be prescribed for monitoring the different points associated with the patient.

Also, in other embodiments, one part of the patient may be allowed to move more compared to another part of the patient. For example, the maximum allowable movement for an arm may be 3 cm, while the maximum allowable movement for a leg may be 5 cm. During the procedure, the treatment may continue when the patient's leg movement is 4 cm. This is better than having one criteria for all patient body parts. For example, if there is only one criteria (e.g., maximum movement=3 cm) for all body parts, in the above example, the treatment may stop when the patient's leg movement is 4 cm. However, this may not be desirable because sometimes a movement by a certain body part of the patient may not impact the treatment. Thus, monitoring multiple points associated with the patient's body with respect to different monitoring criteria is advantageous.

Also, in other embodiments, a patient may be breathing normally using his/her diaphragm in one breathing cycle, but may be breathing using his/her abdomen in another breathing cycle. In such cases, if one monitoring point is at the patient's chest, and another monitoring point is at the patient's abdomen, then both monitoring points may be monitored simultaneously to determine breathing phases of the patient. This way, when the patient is breathing using the diaphragm, the monitoring point at the chest may not vary much in position, and the monitoring point at the chest may be used to determine the breathing phases. On the other hand, when the patient is breathing using the abdomen, the monitoring point at the chest may not vary much in position, and the monitoring point at the abdomen may then be used to determine the breathing phases.

In further embodiments, the determined positions may be analyzed by the patient monitoring system 100 over time to see how stable the various monitoring points are. For example, the patient monitoring system 100 may include a long-term position monitoring module that is configured to receive determined positions over time. The long-term position monitoring module may then calculate a representative position using the determined positions. By means of non-limiting examples, the representative position may be an average position, a mean position, a weighted average position, etc. A small patient movement may be noticeable when comparing the position of the patient with respect to the calculated representative position.

In the above examples, the templates and the input image are described as being generated using the camera 130. In other embodiments, the templates and the input image may be other types of images. For example, in other embodiments, the templates may be generated using a x-ray image, a CT image, a CBCT image, a tomosynthesis image, a PET image, a SPECT image, an MRI image, a PET-CT image, or a SPECT-CT image. Similarly, the input image may be a x-ray image, a CT image, a CBCT image, a tomosynthesis image, a PET image, a SPECT image, an MRI image, a PET-CT image, or a SPECT-CT image. In some embodiments, the templates and the input image may be the same type of image (e.g., camera image). In other embodiments, the templates and the input image may be different types of image (e.g., the templates may be generated using a CT image, and the input image may be a X-ray image).

Embodiments with Depth Sensing Camera

Figure 11A:
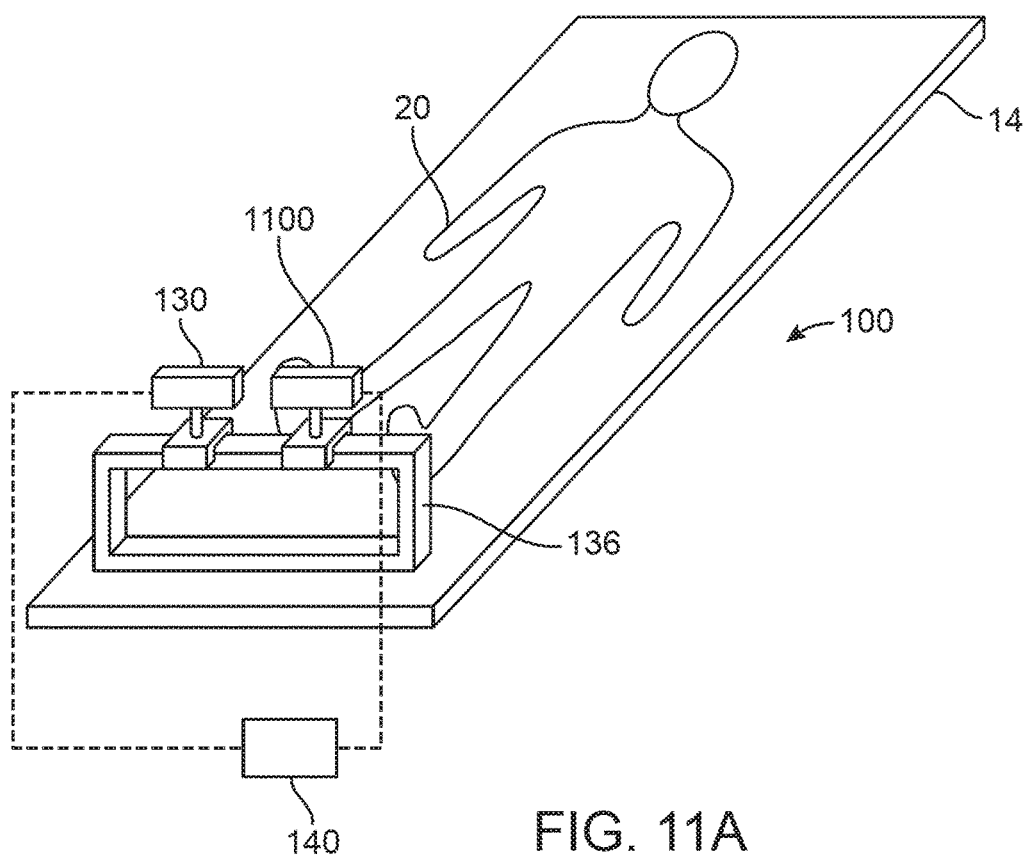
FIG. 11A illustrates another patient monitoring system in accordance with other embodiments.

In some embodiments, the patient monitoring system 100 may optionally include a depth sensing camera. FIG. 11A shows a patient monitoring system 100 that has a depth sensing camera 1100. The patient monitoring system 100 is the same as that of FIG. 2 or FIG. 3, in that it also has the camera 130 and the processing unit 140, except that it further has the depth sensing camera 1100. The depth sensing camera 1100 is configured to sense depths and to generate signals representing the depths. In some embodiments, the depth sensing camera 1100 may use structured light for depth measurement (e.g., a Kinect camera). In other embodiments, the depth sensing camera 1100 may use time-of-flight method for depth measurement (e.g., Mesa SR4000, or the new Microsoft Kinect2 camera). In further embodiments, the depth sensing camera 1100 may be any device that is capable of sensing depth using any known techniques. It should be noted that the term "camera", as used in this specification, may be any device, and should not be limited to a device that provides "image" signals. For example, in some embodiments, the depth sensing camera may be configured to provide depth signals, which may or may not be considered image signals, regardless of whether such depth signals are displayed in image form or not. A depth signal may be any signal indicating a depth or distance, or any signal from which a depth or distance may be derived. By means of non-limiting examples, the signal may be an infrared signal, an ultrasound signal, etc. In some embodiments, the dimensions of the depth sensing camera may be small enough to be non-intrusive to the treatment process when mounted during use. For example, in some embodiments, the camera 1100 may have a dimension of 11 inch×2.5 inch×1.5 inch. In other embodiments, the camera may have other dimensions, such as those larger or smaller than the example provided above, as long as the use of the camera 1100 does not interfere with the medical procedure.

Also, in some embodiments, the depth sensing camera 1100 may be infrared-based, in which cases, the depth may be sensed by the camera using infrared. In some embodiments, such depth sensing camera 1100 may be configured to output infrared video images from which depth images are formed. In some embodiments, these infrared video images may have exactly the same field of view as the depth images. Thus, the infrared video images may be used together with the depth images.

Furthermore, in some embodiments, the depth sensing camera 1100 and the optical camera 130 may be integrated. For example, in some embodiments, the camera may include an infrared emitter, a color sensor, and an infrared depth sensor. The infrared depth sensor is configured to sense depth based on infrared signals output by the infrared emitter. The color sensor is configured to sense visible image.

During use, the depth sensing camera 1100 may be used for segmenting a patient surface for placement of points, so that a plurality of templates may be created based on the points, as similarly discussed. In some embodiments, the depth values obtained from the depth sensing camera 1100 may be thresholded such that pixels with depths corresponding to points within a virtual box surrounding the patient create candidates of regions of interest. Then by feature analysis, these regions may be screened such that the one(s) associated with the patient is retained, and others may be ignored. Inside this region of interest, a grid of points may be setup for patient position monitoring.

The optical camera 130 may be positioned relative to the depth sensing camera 1100 so that it has approximately the same field of view as the depth sensing camera 1100. Then the optical camera 130 may be used for position monitoring. In some embodiments, the grid of points set up on the depth image may be transferred (e.g., based on a transformation using the relative distance and orientation between the optical camera 130 and the depth sensing camera 1100) to the optical camera image pixel coordinates. Then reference templates, one centered on each grid point in the optical image, may be captured and saved in a non-transitory medium. During patient position monitoring, the position of each grid point is tracked in the subsequent video camera frames by matching each reference template to a local search region centered on the corresponding grid point.

In some embodiments, the determined position for a grid point may be compared to a reference position of the same grid point to determine a displacement vector.

In some embodiments, the pixel-domain displacement vector can be converted more precisely from the pixel-domain (i.e., the coordinate of the input image) to a coordinate associated with the patient by back projecting the displacement vector to the actual 3D reference point on the patient (i.e., the point on the 3D surface generated from the depth image).

Also, as similarly discussed, in some embodiments, the determined position may be used by the processing unit 140 to determine whether a certain part of the patient has moved, to monitor a breathing pattern of the patient, to determine whether to generate a signal to stop an operation of the radiation system 10, to gate an operation of the radiation system 10, etc.

During a medical (treatment and/or imaging) procedure, real-time optical input images and real-time depth images are provided by the camera(s), and are transmitted to the processing unit 140. As the procedure continues, the processing unit 140 processes the images at different times to continuously monitor the patient positions.

In some embodiments, the patient monitoring system 100 may include multiple Kinect cameras to get a more complete surface model of the patient (e.g., more complete than the setup in which a camera is mounted at the foot of the patient support with a look-down angle of about 30 degrees, which produces a partial 3D surface model, with un-modeled areas around the neck and upper torso). A complete surface model with corresponding optical images will allow a 3D reference visible image of the patient surface to be determined. This in turn may be used to generate templates that correspond to any arbitrary camera viewing angle during monitoring. Such templates may then be used for monitoring by optical-only cameras placed at multiple positions relative to the patient. For example, two Kinect cameras (or one Kinect camera used sequentially at different positions to generate data from different directions) may be used to generate the complete 3D reference visible image. After the complete 3D reference visible image is obtained, then multiple optical-only cameras may be used for patient monitoring. When one optical camera is blocked by a machine part, one or more other optical cameras may still monitor the patient position.

Figure 11B:
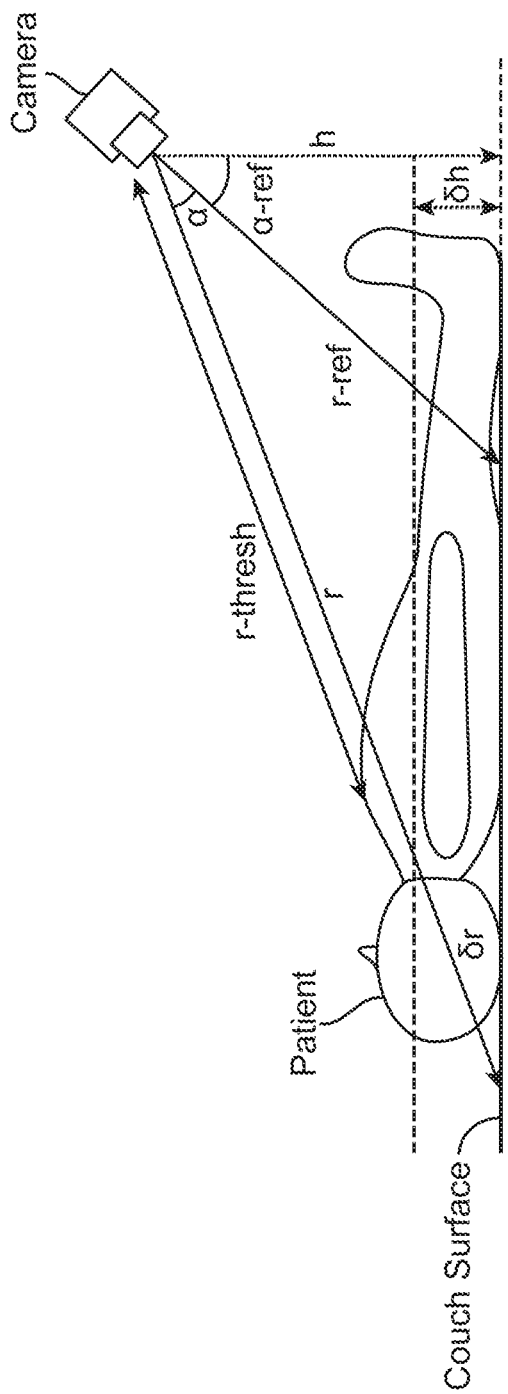
FIG. 11B illustrates a technique for calibrating a camera.

In some embodiments, in order to segment points that are above certain height above the patient support 14, the camera height and orientation relative to the patient support 14 may be calibrated. FIG. 11B illustrates a technique for calibrating the camera in accordance with some embodiments. As shown by the diagram and equations in the figure, the depth value for the rows of the camera may be used to estimate the camera height above the patient support 14, and the look-down angle of a reference row of the depth image pixels. With this information, a table of threshold values may be created that can be used to identify points on the patient surface whose height above the patient support 14 exceeds certain value, δh. The camera calibration estimated parameters may be saved in a non-transitory medium for each camera mounting, and may be reused to generate the transformation parameters that convert the pixel domain displacement to physical space at various points relative to the patient support 14.

In one or more embodiments, the depth image and the optical image may be superimposed/overlaid to obtain a composite image that shows both depth and visible image. Alternatively, the depth image and the optical image may be placed side-by-side to show both images.

In the above embodiments, the patient monitoring system 100 is described as having one camera 130. In other embodiments, the patient monitoring system 100 may include multiple cameras 130 to provide better coverage of the patient.

In further embodiments, instead of using depth sensing camera, the patient monitoring system 100 may include multiple optical cameras separated in a distance to obtain depth information using stereo imaging. In one implementation, optical images from the different optical cameras may be obtained by the processing unit 140, which then calculates the distance to an object being imaged using the images based on triangulation.

Specialized Processing System

Figure 12:
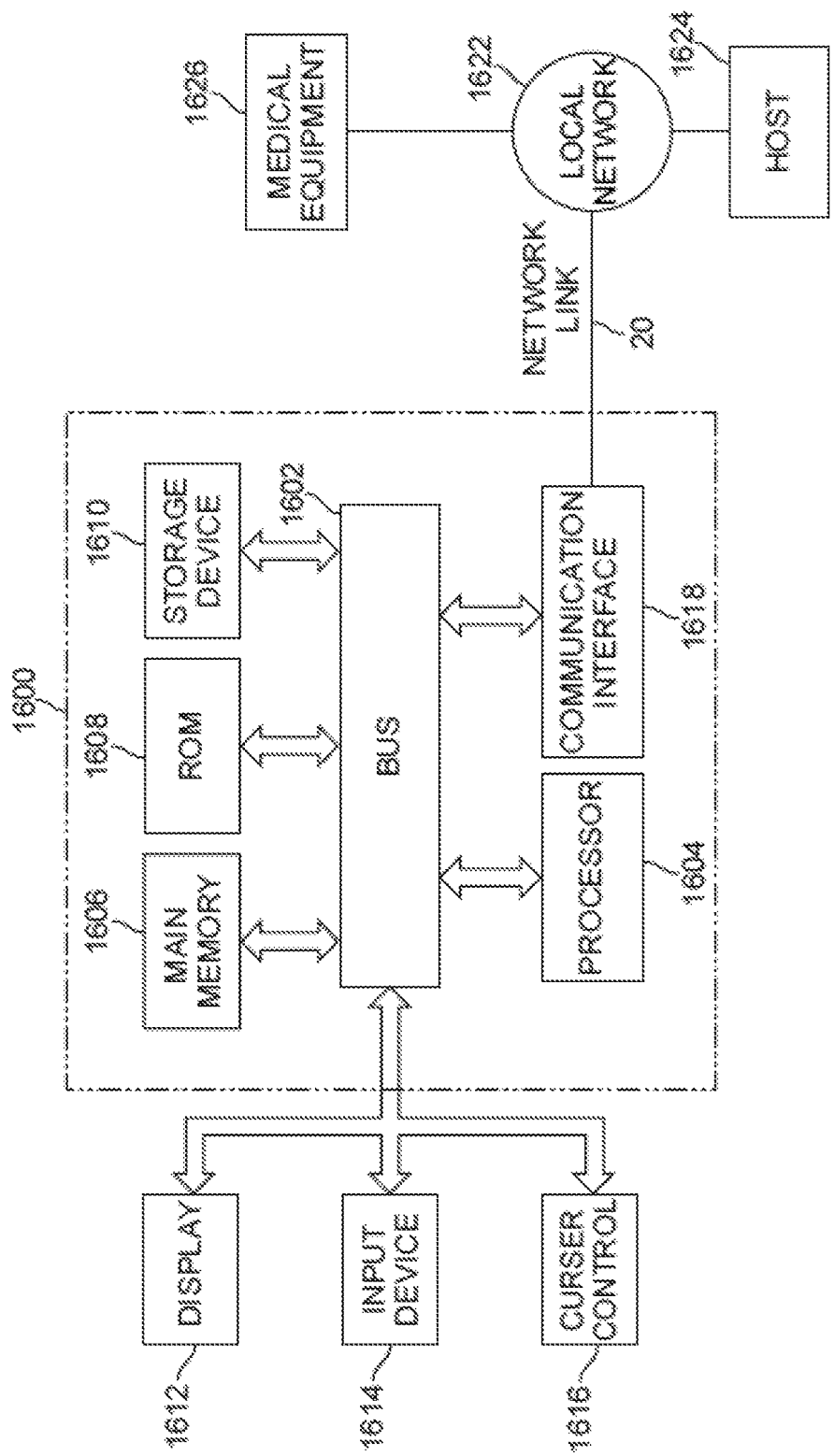
FIG. 12 illustrates a computer system with which embodiments described herein may be implemented.

FIG. 12 is a block diagram illustrating an embodiment of a specialized processing system 1600 that can be used to implement various embodiments described herein. For example, the processing system 1600 may be configured to implement the method of FIG. 4 and/or the method of FIG.

5 in accordance with some embodiments. Also, in some embodiments, the processing system 1600 may be used to implement the processing unit 140 of FIG. 2 and/or the processing unit 54 of FIG. 1. Processing system 1600 includes a bus 1602 or other communication mechanism for communicating information, and a processor 1604 coupled with the bus 1602 for processing information. The processor 1604 may be an example of the processor 54 of FIG. 1, an example of the processing unit 140 of FIG. 2, or an example of any processing unit described herein. The processing system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processing system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processing system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processing system 1600 can be used to perform various functions described herein. According to some embodiments, such use is provided by processing system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another computer-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "computer-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A method of monitoring a patient, comprising:
   obtaining an input image having a plurality of regions of interest by a processing unit; and
   determining a plurality of positions for the respective plurality of regions of interest by the processing unit;
   wherein the act of determining the plurality of positions comprises:
      accessing a plurality of templates, wherein the templates indicate respective features outside the patient that are different from each other;
      comparing the plurality of templates with respective areas in the input image using a comparator in the processing unit; and
      determining the plurality of positions based at least in part on a result of the act of comparing; and
   wherein the method further comprises monitoring, during a medical procedure, different parts of the patient that correspond respectively with the regions of interest in the input image based on the determined plurality of positions.

2. The method of claim 1, wherein the act of comparing comprises performing template matching using the input image and a plurality of templates for the respective regions of interest.

3. The method of claim 1, wherein the act of comparing comprises performing a plurality of cross correlations between the areas in the input image and the plurality of templates.

4. The method of claim 1, further comprising creating the plurality of templates.

5. The method of claim 4, wherein the act of creating the plurality of templates comprises:
   obtaining a reference image;
   determining a plurality of points in the reference image; and
   generating the plurality of templates using pixels in the reference image, such that the templates have respective coordinates that correspond with respective positions of the determined points in the reference image.

6. The method of claim 5, wherein the act of determining the plurality of points in the reference image comprises:
   determining a plane above a patient support supporting the patient;
   determining points on the plane after the plane is determined; and
   transferring the points on the plane to a pixel domain of the reference image.

7. The method of claim 5, wherein the act of determining the plurality of points in the reference image comprises:
   obtaining a depth image;
   processing the depth image to determine a plurality of points in the depth image; and
   transferring the plurality of points in the depth image to a pixel domain of the reference image.

8. The method of claim 7, wherein the act of processing the depth image comprises thresholding depth values in the depth image so that pixels with depths corresponding to points within a virtual box surrounding the patient are included as candidates for the plurality of points in the depth image.

9. The method of claim 5, wherein the act of determining the plurality of points in the reference image comprises:
   obtaining multiple depth images from different directions;
   processing the depth images to determine a three-dimensional surface model;
   determining a plurality of points from the three-dimensional surface model; and
   transferring the plurality of points from the three-dimensional surface model to a pixel domain of the reference image.

10. The method of claim 1, further comprising determining a displacement vector using one of the determined positions.

11. The method of claim 10, further comprising back projecting the displacement vector to a plane above a patient support supporting the patient.

12. The method of claim 11, further comprising determining a vertical displacement and a lateral displacement based on the back projected displacement vector.

13. The method of claim 1, wherein the input image comprises a camera image.

14. The method of claim 1, wherein the positions are determined in substantially real-time to allow real-time monitoring of the patient.

15. The method of claim 1, further comprising generating a signal in response to at least one of the determined positions deviating from a reference position.

16. The method of claim 1, further comprising displaying graphics in a screen representing the determined positions.

17. The method of claim 1, wherein the act of determining the plurality of positions is performed during a radiation delivery.

18. The method of claim 17, wherein the radiation delivery comprises treatment radiation delivery.

19. The method of claim 17, wherein the radiation delivery comprises a delivery of radiation for imaging.

20. An apparatus for monitoring a patient, comprising:
   a processing unit configured for:
      obtaining an input image having a plurality of regions of interest; and
      determining a plurality of positions for the respective plurality of regions of interest;
   wherein the processing unit is configured for determining the plurality of positions by:
      accessing a plurality of templates, wherein the templates indicate respective features outside the patient that are different from each other;
      comparing the plurality of templates with respective areas in the input image using a comparator in the processing unit; and
      determining the plurality of positions based at least in part on a result of the act of comparing; and
   wherein the processing unit is also configured to monitor, during a medical procedure, different parts of the patient that correspond respectively with the regions of interest in the input image based on the determined plurality of positions.

21. The apparatus of claim 20, wherein the processing unit is configured to perform the act of comparing by performing template matching using the input image and a plurality of templates for the respective regions of interest.

22. The apparatus of claim 20, wherein the processing unit is configured to perform the act of comparing by performing a plurality of cross correlations between the areas in the input image and the plurality of templates.

23. The apparatus of claim 20, wherein the processing unit is further configured for creating the plurality of templates, and wherein the apparatus further comprises a non-transitory medium for storing the templates.

24. The apparatus of claim 23, wherein the processing unit is configured to perform the act of creating the plurality of templates by:
  obtaining a reference image;
  determining a plurality of points in the reference image; and
  generating the plurality of templates using pixels in the reference image, such that the templates have respective coordinates that correspond with respective positions of the determined points in the reference image.

25. The apparatus of claim 24, wherein the processing unit is configured to perform the act of determining the plurality of points in the reference image by:
  determining a plane above a patient support supporting the patient;
  determining points on the plane after the plane is determined; and
  transferring the points on the plane to a pixel domain of the reference image.

26. The apparatus of claim 24, wherein the processing unit is configured to perform the act of determining the plurality of points in the reference image by:
  obtaining a depth image;
  processing the depth image to determine a plurality of points in the depth image; and
  transferring the plurality of points in the depth image to a pixel domain of the reference image.

27. The apparatus of claim 26, wherein the processing unit is configured to perform the act of processing the depth image by thresholding depth values in the depth image so that pixels with depths corresponding to points within a virtual box surrounding the patient are included as candidates for the plurality of points in the depth image.

28. The apparatus of claim 24, wherein the processing unit is configured to perform the act of determining the plurality of points in the reference image by:
  obtaining multiple depth images from different directions;
  processing the depth images to determine a three-dimensional surface model;
  determining a plurality of points from the three-dimensional surface model; and
  transferring the plurality of points from the three-dimensional surface model to a pixel domain of the reference image.

29. The apparatus of claim 20, wherein the processing unit is further configured for determining a displacement vector using one of the determined positions.

30. The apparatus of claim 29, wherein the processing unit is further configured for back projecting the displacement vector to a plane above a patient support supporting the patient.

31. The apparatus of claim 30, wherein the processing unit is further configured for determining a vertical displacement and a lateral displacement based on the back projected displacement vector.

32. The apparatus of claim 20, wherein the input image comprises a camera image.

33. The apparatus of claim 20, wherein the processing unit is configured to determine the positions in substantially real-time to allow real-time monitoring of the patient.

34. The apparatus of claim 20, wherein the processing unit is further configured for generating a signal in response to at least one of the determined positions deviating from a reference position.

35. The apparatus of claim 20, further comprising a screen for displaying graphics representing the determined positions.

36. The apparatus of claim 35, wherein the radiation delivery system comprises a treatment radiation delivery system.

37. The apparatus of claim 35, wherein the radiation delivery system comprises a imaging radiation delivery system.

38. The apparatus of claim 20, wherein the processing unit is a part of, or an accessory for, a radiation delivery system.

39. The apparatus of claim 20, further comprising a first optical camera and a second optical camera communicatively coupled to the processing unit.

40. A product having a non-transitory medium storing a set of instructions, an execution of which by a processing unit causes a method for detecting a possible collision in a medical procedure to be performed, the method comprising:
  obtaining an input image having a plurality of regions of interest; and
  determining a plurality of positions for the respective plurality of regions of interest;
  wherein the act of determining the plurality of positions comprises:
    accessing a plurality of templates, wherein the templates indicate respective features outside the patient that are different from each other;
    comparing the plurality of templates with respective areas in the input image; and
    determining the plurality of positions based at least in part on a result of the act of comparing; and
  wherein the method further comprises monitoring, during a medical procedure, different parts of the patient that correspond respectively with the regions of interest in the input image based on the determined plurality of positions.

41. A method of monitoring a patient, comprising:
  obtaining an input image having a plurality of regions of interest by a processing unit, wherein the input image is generated by a device that is configured to sense a characteristic outside the patient; and
  determining a plurality of positions for the respective plurality of regions of interest by the processing unit;
  wherein the act of determining the plurality of positions comprises:
    accessing a plurality of templates, wherein the templates indicate respective features outside the patient that are different from each other;
    comparing the plurality of templates with respective areas in the input image using a comparator in the processing unit; and
    determining the plurality of positions based at least in part on a result of the act of comparing; and
  wherein the method further comprises monitoring, during a medical procedure that involves a delivery of treatment radiation, different parts of the patient that correspond respectively with the regions of interest in the input image based on the determined plurality of positions.

42. The method of claim 41, wherein the plurality of templates is generated using a x-ray image, a CT image, a CBCT image, a tomosynthesis image, a PET image, a SPECT image, an MRI image, a PET-CT image, or a SPECT-CT image.

43. An apparatus for monitoring a patient, comprising:
  a processing unit configured for:
    obtaining an input image having a plurality of regions of interest, wherein the input image is generated by a device that is configured to sense a characteristic outside the patient; and determining a plurality of positions for the respective plurality of regions of interest;
wherein the processing unit is configured for determining the plurality of positions by:
accessing a plurality of templates, wherein the templates indicate respective features outside the patient that are different from each other;
comparing the plurality of templates with respective areas in the input image using a comparator in the processing unit; and
determining the plurality of positions based at least in part on a result of the act of comparing; and
wherein the processing unit is also configured to monitor, during a medical procedure that involves a delivery of treatment radiation, different parts of the patient that correspond respectively with the regions of interest in the input image based on the determined plurality of positions.

44. The apparatus of claim 43, wherein the plurality of templates is generated using a x-ray image, a CT image, a CBCT image, a tomosynthesis image, a PET image, a SPECT image, an MRI image, a PET-CT image, or a SPECT-CT image.

45. A product having a non-transitory medium storing a set of instructions, an execution of which by a processing unit causes a method for detecting a possible collision in a medical procedure to be performed, the method comprising:
obtaining an input image having a plurality of regions of interest, wherein the input image is generated by a device that is configured to sense a characteristic outside a patient; and
determining a plurality of positions for the respective plurality of regions of interest;
wherein the act of determining the plurality of positions comprises:
accessing a plurality of templates, wherein the templates indicate respective features outside the patient that are different from each other;
comparing the plurality of templates with respective areas in the input image; and
determining the plurality of positions based at least in part on a result of the act of comparing; and
wherein the method further comprises monitoring, during a medical procedure that involves a delivery of treatment radiation, different parts of the patient that correspond respectively with the regions of interest in the input image based on the determined plurality of positions.

* * * * *